United States Patent
Whelan

(10) Patent No.: US 12,220,138 B2
(45) Date of Patent: Feb. 11, 2025

(54) ADHESIVE-FREE BONDED BALLOON FOR A BALLOON GUIDE CATHETER WITH MINIMAL OUTER PROFILE

(71) Applicant: Neuravi Limited, Galway (IE)

(72) Inventor: Stephen Whelan, Galway (IE)

(73) Assignee: Neuravi Limited, Galway (IE)

( * ) Notice: Subject to any disclaimer, the term of this patent is extended or adjusted under 35 U.S.C. 154(b) by 262 days.

(21) Appl. No.: 17/807,129

(22) Filed: Jun. 15, 2022

(65) Prior Publication Data

US 2022/0304711 A1 Sep. 29, 2022

Related U.S. Application Data

(62) Division of application No. 16/942,671, filed on Jul. 29, 2020, now abandoned.

(51) Int. Cl.
*A61M 25/10* (2013.01)
*A61B 17/22* (2006.01)

(52) U.S. Cl.
CPC ......... *A61B 17/22* (2013.01); *A61M 25/1034* (2013.01); *A61B 2017/22051* (2013.01)

(58) Field of Classification Search
CPC .......... A61M 25/1034; A61M 25/1002; A61M 25/1018; A61M 25/104; A61B 17/22; A61B 2017/22051
See application file for complete search history.

(56) References Cited

U.S. PATENT DOCUMENTS

| | | | |
|---|---|---|---|
| 4,147,169 A | 4/1979 | Taylor | |
| 4,168,710 A | 9/1979 | Rosenberg | |
| 5,897,537 A | 4/1999 | Berg et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |

(Continued)

FOREIGN PATENT DOCUMENTS

EP 2 719 418 4/2014

OTHER PUBLICATIONS

Copending, co-owned U.S. Appl. No. 16/942,671, filed Jul. 29, 2020.

(Continued)

*Primary Examiner* — Diane D Yabut
*Assistant Examiner* — Christian D Knauss
(74) *Attorney, Agent, or Firm* — Troutman Pepper Locke LLP

(57) ABSTRACT

A balloon guide catheter including a catheter shaft having a reflowable material outer layer. Secured without an adhesive to the catheter shaft is a balloon having a bond interface area with a plurality of punctures defined therein secured about the outer layer of the catheter shaft via seepage of the reflowable material of the outer layer into the plurality of punctures forming a radially outward reflow bond between the catheter shaft and the balloon. Along the bond interface area about the perimeter of the opening in the balloon, a single reflow jacket is secured to the balloon via seepage of the reflowable material of the single reflow jacket into the plural punctures of the balloon forming a radially inward reflow bond. The single reflow jacket is made of a reflowable material and has an opening defined therein aligned with the balloon.

8 Claims, 4 Drawing Sheets

(56) References Cited

U.S. PATENT DOCUMENTS

| | | |
|---|---|---|
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 2003/0078613 A1 | 4/2003 | Heidner |
| 2003/0212360 A1 | 11/2003 | Shkolnik |
| 2007/0016240 A1 | 1/2007 | Warnack et al. |
| 2007/0095474 A1 | 5/2007 | Weller et al. |
| 2008/0077173 A1 | 3/2008 | Flanagan |
| 2008/0255507 A1 | 10/2008 | Mushtaha |
| 2009/0163891 A1 | 6/2009 | Ewing et al. |
| 2010/0268159 A1* | 10/2010 | Engel ............ A61L 29/18 156/60 |
| 2011/0284498 A1 | 11/2011 | Warnack |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0232239 A1 | 8/2017 | Allen et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0117287 A1 | 5/2018 | Krautkremer et al. |
| 2021/0154443 A1 | 5/2021 | Casey et al. |

OTHER PUBLICATIONS

Copending, co-owned U.S. Appl. No. 16/942,684, filed Jul. 29, 2020.

Copending, co-owned U.S. Appl. No. 16/601,185, filed Oct. 14, 2019.

* cited by examiner

ADHESIVE-FREE BONDED BALLOON FOR A BALLOON GUIDE CATHETER WITH MINIMAL OUTER PROFILE

CROSS-REFERENCE TO RELATED APPLICATIONS

This application is a divisional application of U.S. patent application Ser. No. 16/942,671, filed Jul. 29, 2020, which is herein incorporated by reference in its entirety.

BACKGROUND OF THE INVENTION

Field of the Invention

During capture and retrieval of a thrombus, occlusion, or clot in a vessel using an intravascular catheter with a compliant inflatable balloon may be employed to arrest blood flow. The balloon and exterior surface of the catheter shaft of the present inventive balloon guide catheter are secured together at an adhesive free bonding interface area(s) thereby minimizing the outer profile/diameter while optimizing bond strength.

Description of Related Art

Acute ischemic stroke is primarily caused by a thrombotic or embolic occlusion (e.g., blockage) in an artery of the brain. The occlusion is typically caused by a blood clot liberated from another part of the body which travels in an antegrade direction (in the direction of normal blood flow) through the vessel and eventually becomes lodged in a neurovascular artery, where it obstructs blood flow to a region of the brain.

A procedure known as a thrombectomy may be used to remove the thrombus, occlusion, blockage or clot lodged in the vessel using a mechanical retrieval device. During the thrombectomy procedure or treatment a physician or interventionalist endovascularly introduces a guidewire and microcatheter together through the vasculature, typically in an artery located in the groin or the arm or by direct access through the carotid artery. Together the guidewire and microcatheter are advanced to a location facing a proximal side of the targeted clot, blockage or occlusion. Then the guidewire is advanced across the clot, followed by the microcatheter. While in a compressed state, a mechanical thrombectomy device may be guided through the lumen of the microcatheter to the target site. Upon emerging from the microcatheter the mechanical thrombectomy device typically automatically expands to its original enlarged state. Mechanical thrombectomy devices are typically made of a self-expanding biocompatible material such as nickel-titanium. Aspiration through the catheter may accompany or be used in place of the mechanical retrieval device to remove the clot.

During a thrombectomy procedure balloon guide catheters are often employed to arrest blood flow by introducing an inflation fluid into a compliant inflatable balloon. Bonding of the compliant inflatable balloon to the exterior surface of the catheter shaft during manufacture of the balloon guide catheter has two competing criteria, i.e., minimization of the outer profile/diameter at the bonding interface area in which the balloon is mounted to the catheter shaft while maximizing bond strength and integrity.

It is desirable to design an improved balloon guide catheter having an adhesive free bond interface area where the balloon (e.g., compliant, semi-compliant, or non-compliant) is secured to the exterior surface of the catheter shaft to achieve optimum bond strength and integrity while minimizing outer profile or outer diameter.

SUMMARY OF THE INVENTION

An aspect of the present invention is directed to an improved balloon guide catheter to which a balloon is bonded thereto without the use of an adhesive producing maximized bonding strength and integrity while minimizing outer profile or outer diameter.

Another aspect of the present invention is directed to a balloon guide catheter with a catheter shaft having an outer layer made of a reflowable material and a balloon having a bond interface area with a plurality of punctures defined therein secured about the outer layer of the catheter shaft via seepage of the reflowable material of the outer layer into the plurality of punctures forming a radially outward reflow bond between the catheter shaft and the balloon. The balloon being securable to the catheter shaft without the use of an adhesive.

Still another aspect of the present invention is directed to a method for assembling a balloon guide catheter. A plurality of punctures is pierced in a bond interface area of a balloon where securable to an outer layer made of a reflowable material of a catheter shaft. The balloon with the plurality of punctures pierced therein is arranged about the outer layer of the catheter shaft. Along the bond interface area, the reflowable material of the outer layer of the catheter shaft is subject to heat causing it to seep into the plurality of punctures creating a radially outward reflow bond between the outer layer of the catheter shaft and the balloon. Thus, the balloon is securable to the catheter shaft without the use of an adhesive.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which.

DETAILED DESCRIPTION OF THE INVENTION

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "clot" or "blockage" are used interchangeably.

Balloons are typically adhered via adhesive to the exterior surface of the catheter shaft of an assembled balloon guide catheter. The use of an adhesive for securing the balloon poses several disadvantages: increased bond profile and difficulty controlling/constraining the boundaries in which the adhesive remains. It is therefore an aspect of the present invention to eliminate the use of the adhesive (adhesive free bond or non-adhesive bond) where the compliant inflatable balloon is secured to the outer layer of the catheter shaft without sacrificing bond integrity or strength.

Figure 1:
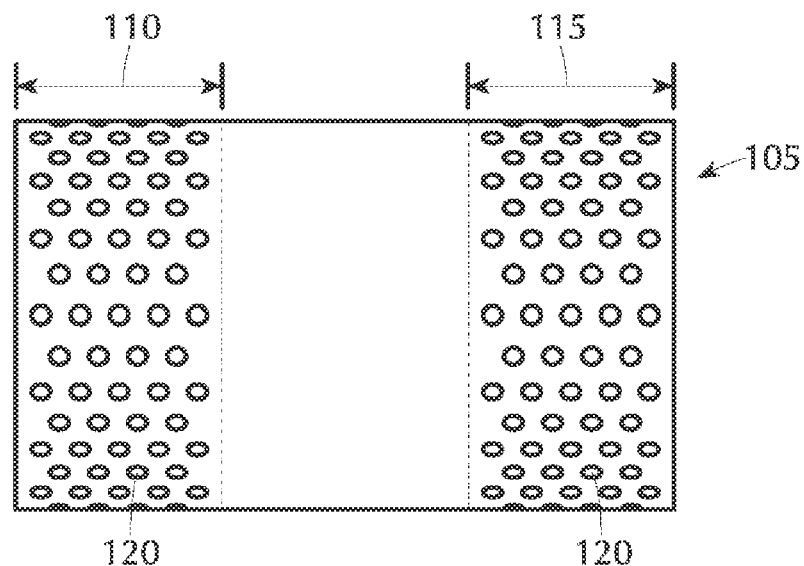
FIG. 1 is a side view of an exemplary compliant inflatable balloon in accordance with the present invention prior to being assembled about a catheter shaft, wherein the compliant inflatable balloon has a proximal bond interface area and an opposite distal bond interface area, each bond interface area having a plurality of puncture holes defined therethrough.

During a thrombectomy procedure balloon guide catheters are often employed to arrest blood flow by introducing an inflation fluid into a compliant inflatable balloon (rather than inflating via pressure) made of an elastomeric material, for example, polyurethane, polyblend, or latex. Its ability to conform to the shape of the vasculature makes the compliant inflatable balloon particularly suited for use in arresting of blood flow. In other applications such as dilating of a vessel or opening an occlusion, balloon guide catheters may employ a non-compliant or semi-compliant balloon that is inflated by pressure, rather than using an inflation fluid. Specifically, non-compliant balloons typically made of polyester or nylon when inflated at a high pressure dilate a vessel or open an occlusion; whereas semi-compliant balloons made of material such as Pebax or higher durometer polyurethanes when inflated in pressure are more compliant than that of non-compliant balloons providing greater flexibility during delivery. Regardless of the type of balloon (compliant, semi-compliant, or non-compliant), bonding of the balloon to the exterior surface of the catheter shaft during manufacture has two competing criteria, i.e., minimization of the outer profile/diameter at the bonding interface area(s) in which the balloon is mounted to the catheter shaft while maximizing bond strength and integrity. By way of example, the present inventive balloon guide catheter is illustrated and described using a compliant inflatable balloon for arresting blood flow through the vessel. It is understood that the present invention is applicable for use with any type of balloon (e.g., compliant, semi-compliant, or non-compliant). FIG. 1 is a side view of a compliant inflatable balloon sleeve 105 in accordance with the present invention prior to assembly about a catheter shaft. Compliant inflatable balloon 105 has a proximal bond interface area 110 and an opposite distal bond interface area 115, wherein the compliant inflatable balloon 105 is securable about the catheter shaft 125 along the proximal and bond interface areas 110, 115, respectively. Each of the proximal and distal bond interface areas has a plurality of punctures 120 (e.g., piercings, holes or openings) therethrough made, for example, with a fine punch tool or other mechanical device. The axial length of each of the proximal and distal bond interface areas 110, 115 with the plural punctures defined therein is preferably approximately 2 mm—approximately 3 mm.

Figure 3:
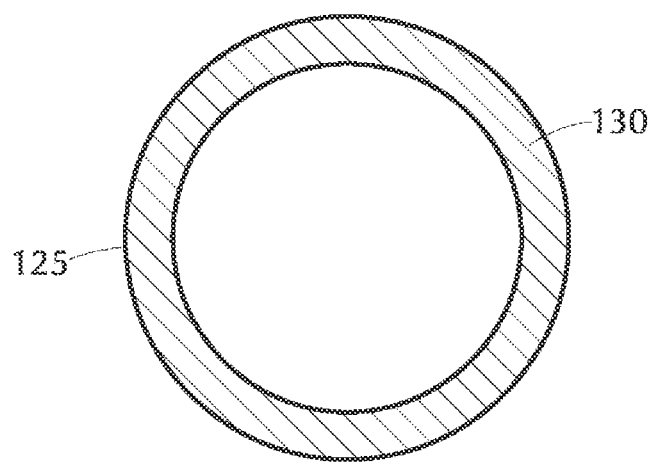
FIG. 3 is a radial cross-sectional view of an outer layer of the catheter shaft in FIG. 2A.
Figure 2A:
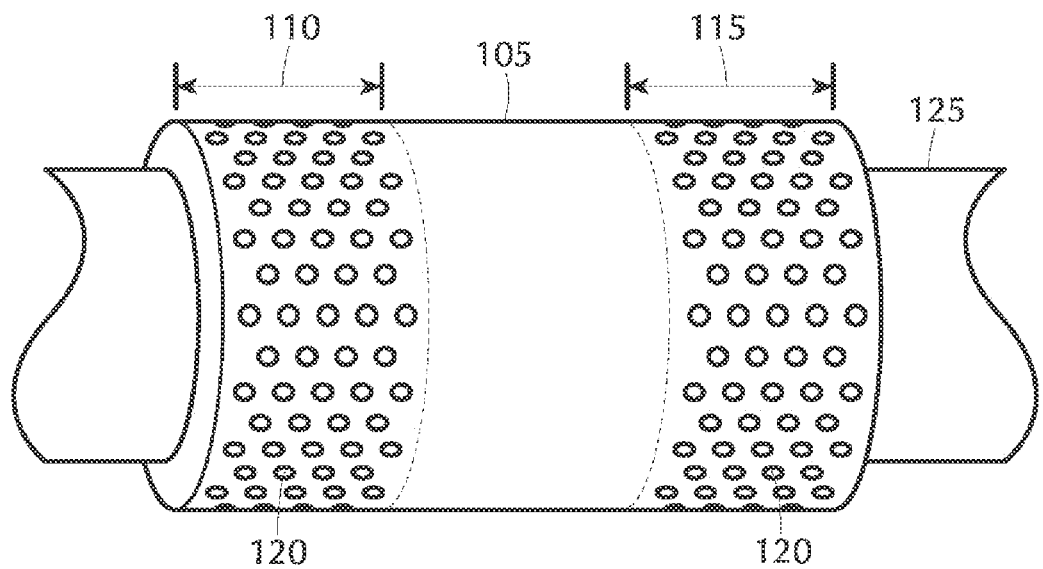
FIG. 2A is a partial side view of an assembled balloon guide catheter including the compliant inflatable balloon of FIG. 1 and a catheter shaft having an outer layer of reflow material reflowing into the plurality of puncture holes defined in the compliant inflatable balloon forming a radially outward reflow bond, wherein the compliant inflatable balloon is depicted in a non-inflated state.
Figure 2B:
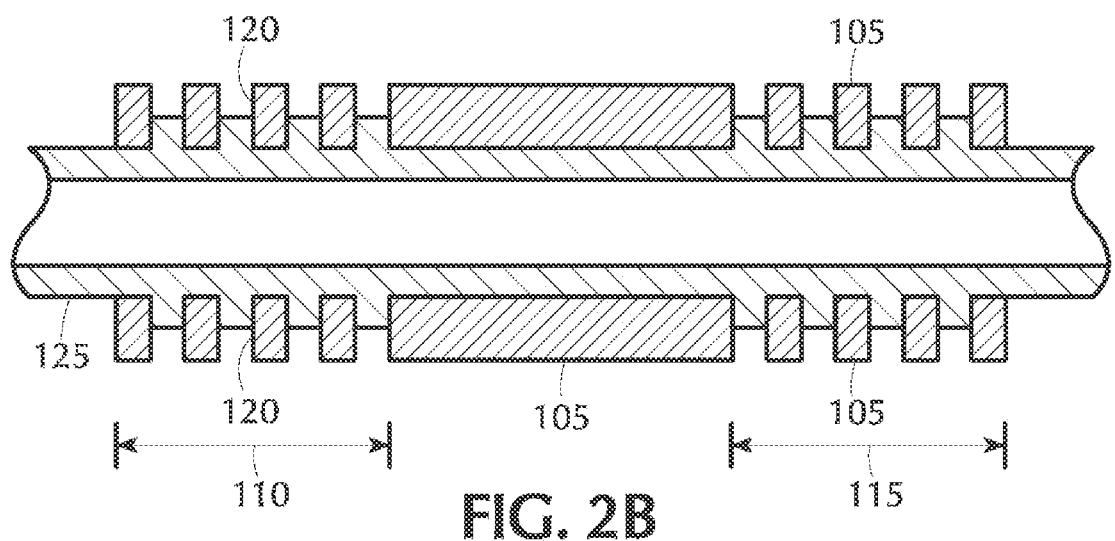
FIG. 2B is a longitudinal cross-sectional view of the assembled balloon guide catheter of FIG. 2A illustrating the radially outward reflow bond formed by seepage of the outer layer of reflow material into the plurality of puncture holes defined in the compliant inflatable balloon.

The compliant inflatable balloon 105 with the plural punctures 120 made in each of the proximal and distal bond interface areas 110, 115, respectively, is positioned exteriorly about a catheter shaft 125 as shown in FIGS. 2A & 2B. A radial cross-sectional view through an exemplary catheter shaft 125 illustrating its outer layer 130 is represented in FIG. 3. The outer layer 130 of the catheter shaft is made of a reflowable material, preferably one that includes medical grade thermoplastic polyurethane (TPU) (e.g., Tecoflex®—a medical-grade Aliphatic Polyether-based Thermoplastic Polyurethane). Catheter shaft 125 may be designed, as desired, to comprise any number of one or more inner layers disposed radially inward of the outer layer 130.

Specific regions of the compliant inflatable balloon 105, preferably restricted only to those areas to be bonded to the catheter shaft (e.g., proximal and distal bond interface areas 110, 115 of the balloon sleeve; or a perimeter of a balloon patch), are subject to heat (e.g., thermal and/or laser generated) causing reflow/melting of the outer layer 130 of the catheter shaft 125 which seeps/oozes upwards through the punctures 120 (piercings, holes, openings) forming a radially outward reflow bond therebetween. By way of illustrative example, heated jaws may be applied only about those areas of the compliant inflatable balloon to be bonded thereby restricting the heat to a certain area or distance.

To further strengthen the bond of the balloon to the catheter shaft, an additional step may be performed in sequence or simultaneously with the forming of the radially outward reflow bond to create a supplemental radially inward reflow bond using one or more reflow jacket(s)/sleeve(s) made of a reflow material (a material that preferably includes medical grade thermoplastic polyurethane (TPU)). Preferably, the reflow material of the one or more reflow jacket(s)/sleeve(s) and that of the outer layer of the catheter shaft is the same to ensure the reflow of both materials when subject to heat at a predetermined temperature. Thus, the reflow bond is created both radially inward and radially outward of the proximal and distal interface bond areas of the compliant inflatable balloon. That is, when heated the reflow/melted outer layer 130 of the catheter shaft 125 seeps radially outwards through the punctures 120 creating a radially outward reflow bond, while the reflow/melted reflow jackets/sleeves 135, 140 ooze radially inwards through the punctures 120 creating a radially inward reflow bond. The enhanced reflow bonds (radially inward and radially outward) created between the reflowing/melting of the material for the reflow jackets/sleeves 135, 140 and outer layer 130 of the catheter shaft 125 into the punctures 120 on either side of the compliant inflatable balloon 105 optimizes bond integrity and strength while minimizing the potential for leakage without increasing the outer diameter/profile.

Figure 4A:
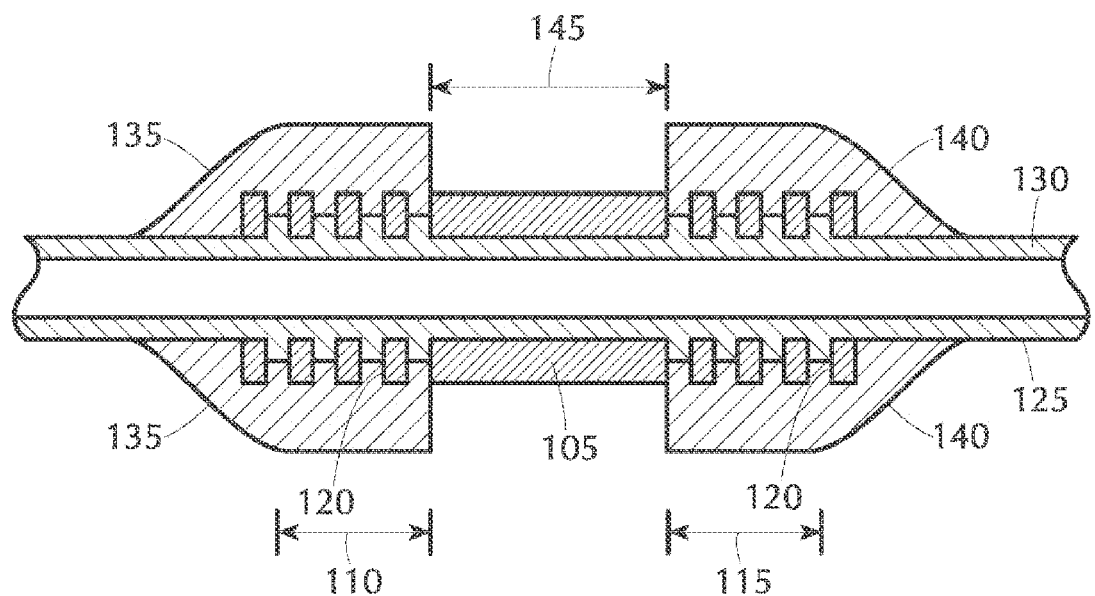
FIG. 4A is a partial longitudinal cross-sectional view of an alternative configuration with two reflow jackets/sleeves separate from one another in an axial direction to form a 360° radial gap therebetween, each reflow jacket/sleeve securing beneath a respective proximal and distal bond interface area of the compliant inflatable balloon to the outer layer of the catheter shaft, wherein the compliant inflatable balloon is represented in a non-inflated state.
Figure 4B:
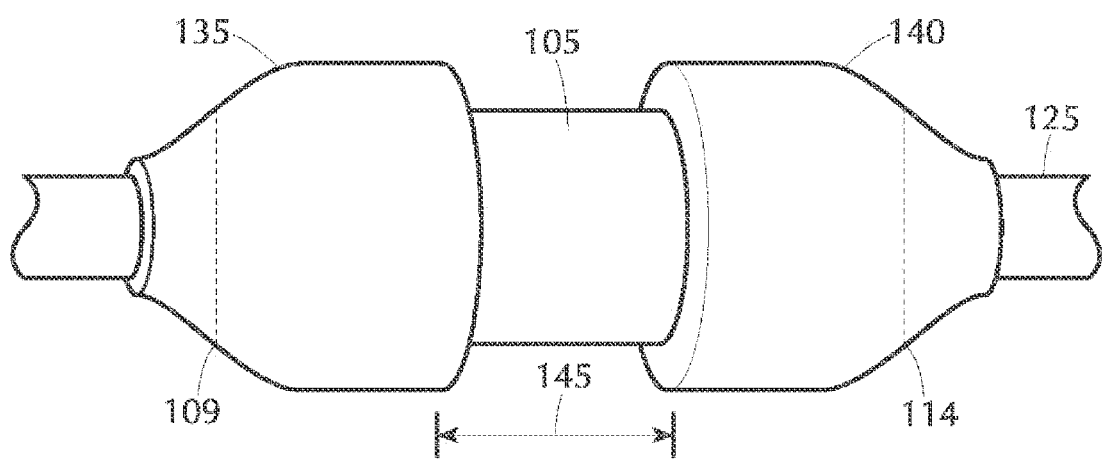
FIG. 4B is a side view of the assembled catheter of FIG. 4A.

In one configuration shown in FIGS. 4A & 4B, two reflow jackets/sleeves are employed, i.e., one reflow jacket/sleeve placed about each of the proximal and distal bond interface areas 110, 115 of the compliant inflatable balloon sleeve 105. That is, a proximal reflow jacket/sleeve 135 is disposed about the compliant inflatable balloon coinciding with/covering the proximal bond interface area 110, while a distal reflow jacket/sleeve 140 is positioned about the compliant inflatable balloon coinciding with/covering the distal bond interface area 115. Dashed lines in the side view of FIG. 4B depict the proximal and distal edges 109, 114, respectively, of the compliant inflatable balloon 105 covered by the respective proximal and distal reflow jackets/sleeves 135, 140. A 360° radial gap 145 is formed between proximal and distal reflow jackets/sleeves 135, 140 separated in an axial/longitudinal direction from one another. Preferably, the two reflow jackets/sleeves are each made of the same material as that of the outer layer 130 of the catheter shaft 125 to ensure reflow when heated at a predetermined temperature. When inflated with an inflation fluid, the exposed 360° radial region of the compliant inflatable balloon patch 105 expands through the 360° radial gap 145 forming a radial bulge or radial inflation (e.g., tire).

Figure 5A:
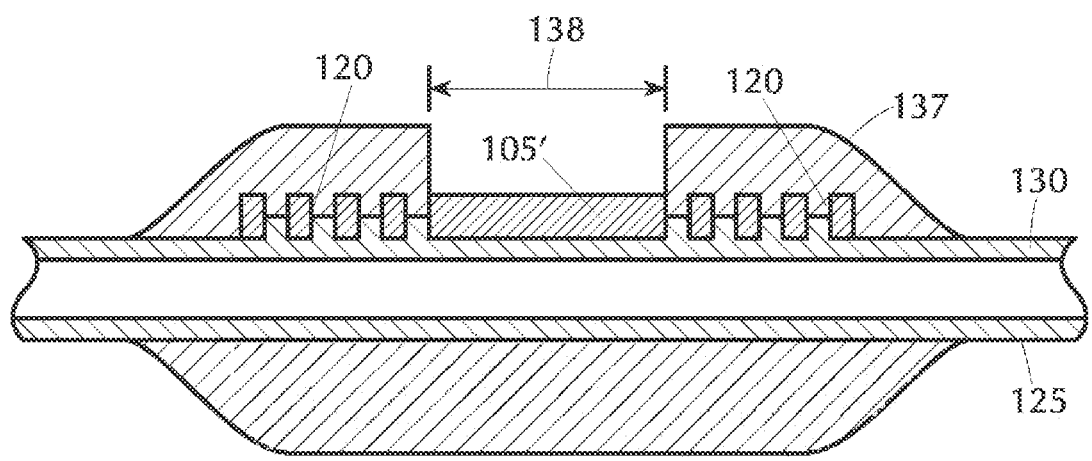
FIG. 5A is a partial longitudinal cross-sectional view of still another design with a single reflow jacket/sleeve having a cut-out or opening defined therein aligned with a compliant inflatable balloon patch secured beneath to the catheter shaft, wherein the compliant inflatable balloon is depicted in a non-inflated state.
Figure 5B:
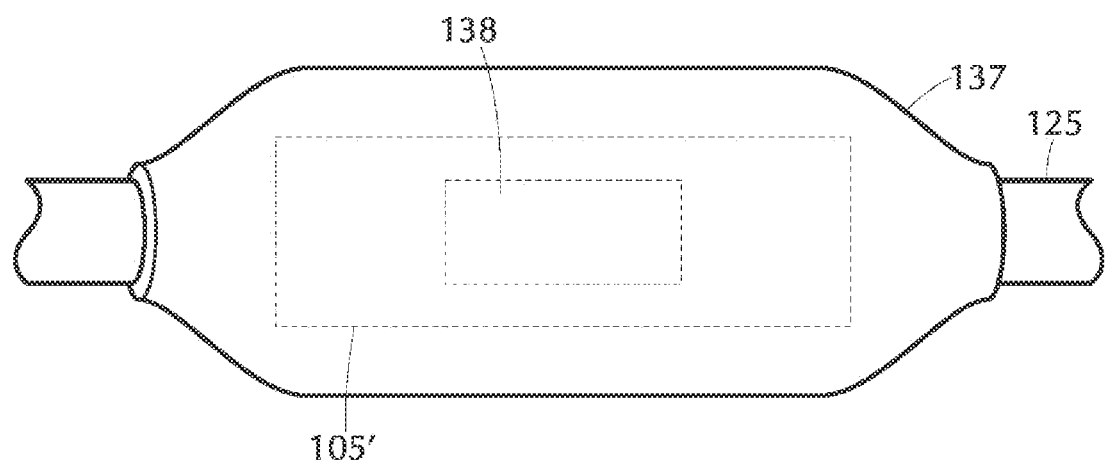
FIG. 5B is a top view of the assembled catheter of FIG. 5A.

An alternative design employing a single reflow jacket/sleeve 137 with a cut-out or opening 138 defined therein is set forth in the longitudinal cross-sectional and top views of FIGS. 5A and 5B, respectively. In this configuration since a single reflow jacket/sleeve 137 is used, the cut-out or opening 138 defined in the axial/longitudinal side thereof extends less than 360° radially. The dimensions (both axially/longitudinally and radially/laterally) of the cut-out or opening 138 is slightly smaller than a perimeter of the compliant inflatable balloon patch 105'. During assembly the single reflow jacket/sleeve 137 is aligned with and disposed radially outward of the compliant inflatable balloon patch 105' exposing a central region of the compliant inflatable balloon patch 105' through the cut-out or opening 138. When inflated with an inflation fluid, the exposed central region of the compliant inflatable balloon patch 105' expands through the cut-out or opening 138 forming a side bulge or side inflation.

The different aspects, features, designs and configurations of the invention may be combined, as desired, for a given intravascular catheter with the intended goals of enhancing the integrity and strength of the bond between the balloon and the catheter shaft, while simultaneously minimizing the outer profile or outer diameter of the assembled catheter.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A balloon guide catheter comprising:
   a catheter shaft having an outer layer made of a reflowable material;
   a balloon having a bond interface area with a plurality of punctures defined therein secured about the outer layer of the catheter shaft via seepage of the reflowable material of the outer layer into the plurality of punctures forming a radially outward reflow bond between the catheter shaft and the balloon; wherein the balloon is secured to the catheter shaft without an adhesive; and
   a single reflow jacket made of a reflowable material; the single reflow jacket having an opening defined therein aligned with the balloon; and wherein along the bond interface area of the balloon about a perimeter of the opening, the single reflow jacket is secured to the balloon via seepage of the reflowable material of the single reflow jacket into the plurality of punctures of the balloon forming a radially inward reflow bond.

2. The balloon guide catheter according to claim 1, wherein the reflowable material of the single reflow jacket is the same as the reflowable material of the outer layer of the catheter shaft.

3. The balloon guide catheter according to claim 1, wherein the opening in the single reflow jacket is arranged radially outward relative to the catheter shaft.

4. The balloon guide catheter according to claim 1, wherein the opening in the single reflow jacket extends less than 360 degrees radially about the catheter shaft.

5. A method for assembling a balloon guide catheter, the method comprising the steps of:
   piercing a plurality of punctures in a bond interface area of a balloon where securable to an outer layer made of a reflowable material of a catheter shaft;
   arranging the balloon with the plurality of punctures pierced therein about the outer layer of the catheter shaft;
   subjecting to heat along the bond interface area causing the reflowable material of the outer layer of the catheter shaft to seep into the plurality of punctures creating a radially outward reflow bond between the outer layer of the catheter shaft and the balloon; wherein the balloon is secured to the catheter shaft without an adhesive; and
   positioning a single reflow jacket made of a reflowable material disposed about the balloon covering the bond interface area; the single reflow jacket having an opening defined therein aligned with the balloon;
   and wherein along the bond interface area of the balloon about a perimeter of the opening in the balloon, securing the single reflow jacket to the balloon by heating of the reflowable material of the single reflow jacket causing seepage into the plurality of punctures of the balloon forming a radially inward reflow bond.

6. The method according to claim 5, wherein the reflowable material of the single reflow jacket is the same as the reflowable material of the outer layer of the catheter shaft.

7. The method according to claim 5, wherein the opening in the single reflow jacket is arranged radially outward relative to the catheter shaft.

8. The method according to claim 5, wherein the opening in the single reflow jacket extends less than 360 degrees radially about the catheter shaft.

* * * * *